(12) United States Patent
Bruder et al.

(10) Patent No.: US 8,768,030 B2
(45) Date of Patent: Jul. 1, 2014

(54) CT MEASUREMENT WITH MULTIPLE X-RAY SOURCES

(75) Inventors: Herbert Bruder, Höchstadt (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 510 days.

(21) Appl. No.: 13/020,256

(22) Filed: Feb. 3, 2011

(65) Prior Publication Data

US 2011/0188724 A1 Aug. 4, 2011

(30) Foreign Application Priority Data

Feb. 4, 2010 (DE) .......................... 10 2010 006 774

(51) Int. Cl.
*G06K 9/00* (2006.01)
*A61B 6/00* (2006.01)
*A61B 6/03* (2006.01)
*G06T 11/00* (2006.01)

(52) U.S. Cl.
CPC ................. *A61B 6/481* (2013.01); *A61B 6/482* (2013.01); *A61B 6/504* (2013.01); *A61B 6/4014* (2013.01); *A61B 6/466* (2013.01); *G06T 2211/424* (2013.01); *G06T 11/006* (2013.01); *A61B 6/032* (2013.01)
USPC ................. 382/131; 382/132; 378/9; 378/10; 378/11; 378/12; 378/13; 378/92

(58) Field of Classification Search
CPC ................. G06T 11/003; G06T 11/005; G06T 2207/10072; G06T 2207/10081; G06T 2211/424; A61B 6/03; A61B 6/032; A61B 6/0033

USPC ......... 382/131, 132; 378/9, 10, 11, 12, 13, 92
See application file for complete search history.

(56) References Cited

U.S. PATENT DOCUMENTS 5,848,114 A * 12/1998 Kawai et al. ...................... 378/4
2007/0086564 A1* 4/2007 Bruder et al. ..................... 378/9

(Continued)

FOREIGN PATENT DOCUMENTS

CN 1985765 A 6/2007
CN 101313214 A 11/2008

(Continued)

OTHER PUBLICATIONS

Sunnegardh, Johan. Iterative Filtered Backprojection Methods for Helical Cone-Beam CT. Diss. Linkoping Universitet, 2009. Print.*

(Continued)

*Primary Examiner* — Michael A Newman
(74) *Attorney, Agent, or Firm* — Harness, Dickey & Pierce (57) ABSTRACT

A method is disclosed for reconstructing image data of an examination object from measurement data of a computed tomography system, the examination object having been irradiated simultaneously by a number of X-ray sources while the measurement data was being acquired so that different projections of the examination object associated with the number of X-ray sources were acquired simultaneously for each detector element. In at least one embodiment, different iteration images of the examination object are determined one after the other from the measurement data by way of an iterative algorithm, a computation operation being employed with the iterative algorithm, which is applied to the iteration images and takes the presence of the number of X-ray sources into account.

18 Claims, 3 Drawing Sheets

(56) References Cited

U.S. PATENT DOCUMENTS

| | | | |
|---|---|---|---|
| 2008/0205729 A1* | 8/2008 | Ziegler et al. | 382/131 |
| 2008/0240340 A1* | 10/2008 | Bruder et al. | 378/7 |
| 2009/0196393 A1* | 8/2009 | Wang et al. | 378/4 |
| 2010/0166140 A1 | 7/2010 | Proksa | |
| 2010/0329532 A1* | 12/2010 | Masuda et al. | 382/132 |
| 2011/0282181 A1* | 11/2011 | Wang et al. | 600/407 |

FOREIGN PATENT DOCUMENTS

| | | |
|---|---|---|
| CN | 101505660 A | 8/2009 |
| WO | WO 2007-038306 | 4/2007 |
| WO | WO 2008-024586 | 2/2008 |
| WO | WO 2009084581 A1 | 7/2009 |

OTHER PUBLICATIONS

Wang, et al. "A Scheme for Multisource Interior Tomography." Am. Assoc. Phys. Med. 36.8 (2009): 3575-3581. Print.*

Sunnegardh, Iterative Filtered Backprojection Methods for Helical Cone-Beam CT. Diss. Linkoping Universitet, 2009. Print.*

Baek, et al. "Direct two-dimensional reconstruction algorithm for an inverse-geometry CT system." Medical Physics. 36.2 (2009): 394-401. Print.*

Office Action by the German Patent Office dated Sep. 17, 2010 for 10 2010 006 774.1-35.

Article by K. Mueller et al : Fast implementations of algebraic methods for three-dimensional reconstruction of cone-beam data:, IEEE Trans. Med. Imag. 18(6): 538-548, 1999, Others, 1999.

Article by P.M. Joseph: "An improved algorithm for reprojection rays through pixel images," IEEE Trans. Med. Imag. 1:193-196, 1982; Others; 1982.

Article by L. Landweber from American Journal of Mathematics, vol. 73, No. 3 (Jul. 1951) 615-624; An Iteration Formula for Fredholm Integral Equations of the First Kind; Others; 1951.

Wang et al; " A Scheme for Multisource Interior Tomography"; Am. Assoc. Phys. Med; Med. Phys 36(8); pp. 3575-3581; 2009.

Zhuang Tianzuo; "CT theory and algorithm" Shanghai Jiao Tong University Press; pp. 77-97; 1992; CN; Aug. 31, 1992.

* cited by examiner

CT MEASUREMENT WITH MULTIPLE X-RAY SOURCES

PRIORITY STATEMENT

The present application hereby claims priority under 35 U.S.C. §119 on German patent application number DE 10 2010 006 774.1 filed Feb. 4, 2010, the entire contents of which are hereby incorporated herein by reference.

FIELD

At least one embodiment of the invention generally relates to a method for acquiring measurement data with a computed tomography system and/or a method for reconstructing image data of an examination object from said measurement data.

BACKGROUND

Methods for scanning an examination object with a CT system are generally known. These use for example circular scans, sequential circular scans with advance or spiral scans. Other types of scan that are not based on circular movements are also possible, for example scans with linear segments. At least one X-ray source and at least one detector opposite it are used to record absorption data of the examination object from different recording angles and the absorption data thus collected or projections are computed by way of appropriate reconstruction methods into sectional images through the examination object.

A method referred to as filtered back projection FBP is currently used as the standard method for reconstructing computed tomography images from X-ray CT data sets of a computed tomography device (CT device), in other words from the acquired projections. Following the data acquisition a step referred to as "rebinning" is performed in which the data generated by the beam widening out in the shape of fan from the source is re-ordered in such a way that it is present in a form as though the detector were struck by X-ray beams converging in a parallel manner onto the detector. The data is then transformed into the frequency domain. Filtering takes place in the frequency domain and the filtered data is then back transformed. With the aid of the thus re-sorted and filtered data a back projection is then performed onto the individual voxels within the volume of interest.

Iterative reconstruction methods have recently been developed. With such an iterative reconstruction method initial image data is first reconstructed from the projection measurement data. A convolution back projection method for example can be used for this purpose. A projector or projection operator intended to map the measurement system mathematically as efficiently as possible is then used to generate synthetic projection data from this initial image data. The difference compared with the measurement signals is then back projected with the operator adjoined to the projector and a residual image is thus reconstructed, which is used to update the initial image. The updated image data can be used in turn to generate new synthetic projection data in a subsequent iteration step with the aid of the projection operator, form the difference compared with the measurement signals again from this and calculate a new residual image which can be used again to improve the image data of the current iteration stage, etc. With such a method it is possible to reconstruct image data that features relatively good image sharpness and yet still has low image noise.

The quality of CT images increases with the number of X-ray quanta emitted by the X-ray source during measurement. However this number is limited by the structure of the X-ray source and cannot therefore be raised arbitrarily.

SUMMARY

At least one embodiment of the invention is directed to demonstrating a method for reconstructing CT images, in which an attempt is made to irradiate the examination object with an increased number of X-ray quanta while the measurement data is being acquired. A corresponding control and computation unit, CT system, computer program and computer program product are also to be demonstrated in other embodiments. A corresponding method for data acquisition is also to be presented in another embodiment.

At least one embodiment is directed to a method, and at least one embodiment is directed to a control and computation unit, CT system, computer program and/or computer program product. Advantageous embodiments and developments form the subject matter of subclaims.

With at least one embodiment of the inventive method for reconstructing image data of an examination object from measurement data of a computed tomography system, the examination object has been irradiated simultaneously beforehand by a number of X-ray sources while the measurement data was being acquired so that different projections of the examination object associated with the number of X-ray sources were acquired simultaneously for each detector element. An iterative algorithm is used to determine different iteration images of the examination object one after the other from the measurement data, with a computation operation being employed with the iterative algorithm, which is applied to the iteration images and takes the presence of the number of X-ray sources into account.

With conventional CT systems an X-ray source is assigned to each detector, so that the detector acquires the projections of the X-ray source. If a number of X-ray sources are present, a number of detectors are also employed; this is the case with what are known as "dual source" CT devices. In contrast to such known systems according to at least one embodiment of the invention two or more X-ray sources are employed, the projections of which are acquired simultaneously by the same detector. A detector element therefore measures a signal made up of projections from at least a first and a second X-ray source. The simultaneous nature of data acquisition means that it is not possible to separate the signals of the two X-ray sources at the detector.

The number of X-ray sources are preferably identical sources. This means that the X-ray sources emit X-ray radiation of roughly identical spectral distribution. Separation of the measurement signals originating from the number of X-ray sources is therefore also not possible in this instance based on the quantum energies.

There are various options for the geometric arrangement of the X-ray sources. They must however be arranged and aligned relative to one another and to the detector in such a manner that the radiation from the number of X-ray sources strikes the detector elements. This is preferably the case for all the elements of the detector.

The measurement data acquired by simultaneous irradiation of the examination object with the number of X-ray sources is used to reconstruct an image of the examination object. This CT image reconstruction takes place iteratively: further iteration images are calculated based on a first iteration image. The last iteration image, which is determined for example based on a termination criterion of the iteration algorithm, can be output as the resulting image.

During iteration a computation operation is used, which takes into account that a number of X-ray sources have irradiated the examination object during measurement. This computation operation is applied to the respective iteration image. In particular the computation operation can comprise at least one operator, which maps the measurement geometry while the measurement data is being acquired. The measurement geometry includes, inter alia, the positions of the X-ray sources in relation to one another and to the detector. The computation operation is preferably used to calculate projection data from the respective iteration image. The calculated projection data is data corresponding to measurement data but determined by calculation rather than based on a measurement process. It can therefore be referred to as "synthetic" measurement data.

Since the calculated projection data corresponds to the measurement data, it can be linked to the measurement data. This link can in particular consist of a subtraction so that the calculated projection data is compared with the measurement data as a result.

In an embodiment of the invention, image data is calculated from the linking of the projection data to the measurement data. An algorithm for CT image reconstruction known per se can be employed for this purpose. If the linking of the projection data to the measurement data is a subtraction, the image data is also differential data.

It is advantageous to link this image data to the iteration image of the previous iteration. This link can consist in particular of an—optionally weighted—subtraction or addition, so that the iteration image of the previous iteration is modified and improved by the image data. It is advantageous here before linking to apply a non-linear regularization function to the iteration image of the previous iteration. This step serves to improve convergence of the iteration algorithm.

In an embodiment of the invention projection data is calculated by way of the computation operation from the linking of the image data to the iteration image of the last iteration. This projection data again corresponds to the projection data described above, being associated with the next iteration. The iterative method can therefore be continued as described above with said projection data.

According to a development of at least one embodiment of the invention the number of X-ray sources move around the examination object while the measurement data is being acquired. To this end it is possible to employ the X-ray sources generally used with third-generation CT systems. It is however also possible for the number of X-ray sources to be produced by activating a number of elements of an X-ray source comprising a plurality of elements. These X-ray sources comprising the individual elements can also be moved during measurement; alternatively it is possible for them to remain still and for the examination object to be illuminated from different directions by activating elements differently over time.

With at least one embodiment of the inventive method for acquiring measurement data of an examination object with a computed tomography system a number of X-ray sources are provided to acquire measurement data. While the measurement data is being acquired, the examination object is irradiated simultaneously by the number of X-ray sources in such a manner that different projections of the examination object associated with the number of X-ray sources are acquired simultaneously for each detector element. The above statements relating to the image reconstruction method are correspondingly applicable.

At least one embodiment of the inventive control and computation unit is used to reconstruct image data of an examination object from measurement data of a CT system and/or to control measurement data acquisition of a CT system. It comprises a program memory for storing program code, with program code—optionally among other things—being present which is suitable for executing a method of the type described above, i.e. controlling the measurement data acquisition process and/or performing image reconstruction. At least one embodiment of the inventive CT system comprises such a control and computation unit. It can also contain other components, which are required for example to acquire measurement data.

At least one embodiment of the inventive computer program has program code segments that are suitable for performing the method of the type described above, when the computer program is executed on a computer.

At least one embodiment of the inventive computer program product comprises program code segments stored on a computer-readable data medium, which are suitable for performing the method of the type described above when the computer program is executed on a computer.

BRIEF DESCRIPTION OF THE DRAWINGS

The invention is described in more detail below with reference to an example embodiment. In the drawings.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
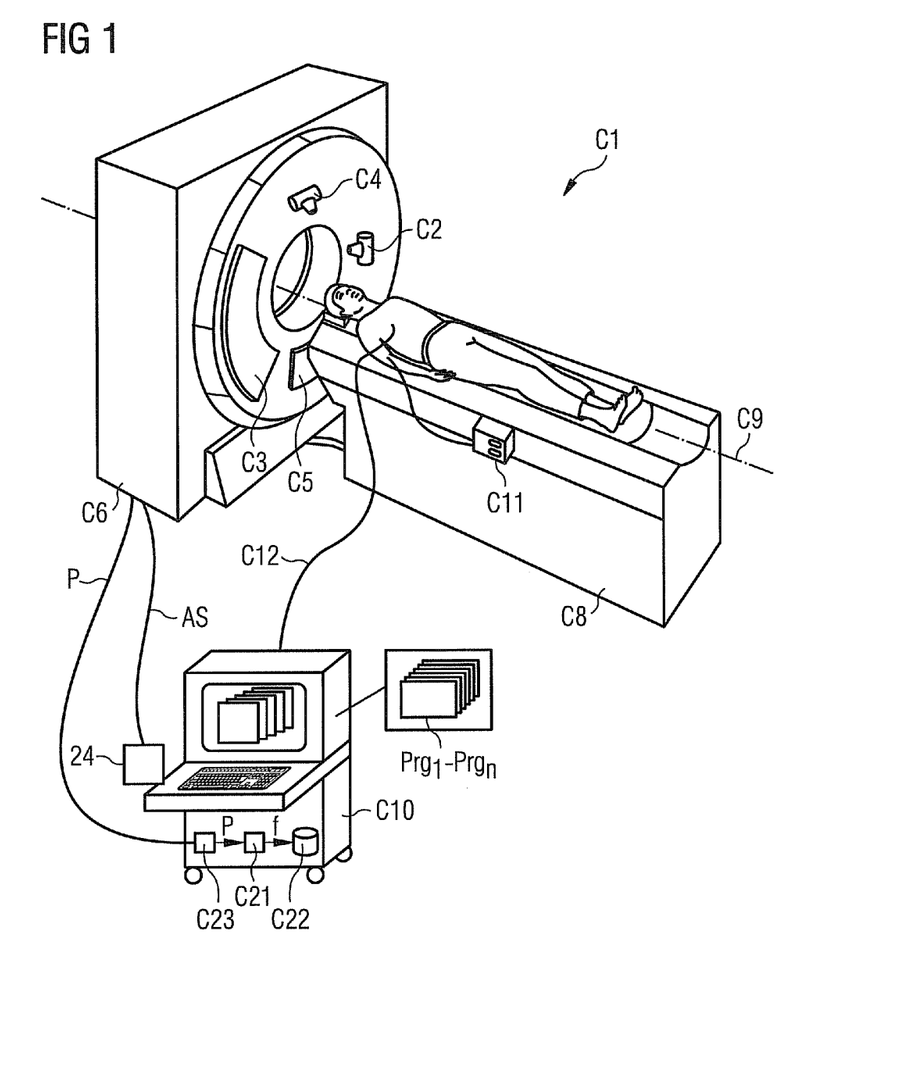
FIG. 1: shows a first schematic diagram of an example embodiment of a computed tomography system having an image reconstruction component.

FIG. 1 first shows a schematic diagram of a first computed tomography system C1 having an image reconstruction facility C21. This is a CT device of what is known as the third generation, to which embodiments of the invention is not however restricted. Located in the gantry housing C6 is a closed gantry (not shown here), on which a first X-ray tube C2 with a detector C3 opposite it is disposed. A second X-ray tube C4 with a detector C5 opposite it is optionally disposed in the CT system shown here, the additionally available emitter/detector combination allowing a higher temporal resolution to be achieved, or it being possible for "dual energy" examinations also to be performed using different X-ray energy spectra in the emitter/detector systems.

The CT system C1 also has a patient couch C8, on which a patient can be moved during the examination along a system axis C9, also referred to as the z-axis, into the measurement field, it being possible for the scanning operation itself to take place as a simple circular scan without patient advance in the examination region of interest. The movement of the patient couch C8 relative to the gantry is brought about by a suitable motor. During such movement the X-ray source C2 and/or C4 rotates about the patient. The detector C3 and/or C5 follows in a parallel manner opposite the X-ray source C2 and/or C4 to acquire projection measurement data which is then used to reconstruct sectional images. As an alternative to a sequential scan, in which the patient is moved gradually through the examination field between the individual scans, it is of course also possible to perform a spiral scan, in which the patient is moved continuously through the examination field between X-ray tube C2 and/or C4 and detector C3 and/or C5 along the system axis C9 while being scanned in a rotating manner with the X-ray radiation. The movement of the patient along the axis C9 and the simultaneous rotation of the X-ray source C2 and/or C4 in a spiral scan produces a helical path for the X-ray source C2 and/or C4 relative to the patient during measurement. This path can also be achieved by moving the gantry along the axis C9 while the patient remains still. It is further possible to move the patient to and fro continuously and periodically between two points.

The CT system 10 is controlled by a control and computation unit C10 having computer program code $Prg_1$ to $Prg_n$ present in a memory. It should be noted that such computer program codes $Prg_1$ to $Prg_n$ can also be contained on an external storage medium and be loaded into the control and computation unit C10 as required.

Acquisition control signals AS can be transmitted from the control and computation unit C10 by way of a control interface 24, to activate the CT system C1 according to certain measurement protocols. The acquisition control signals AS here relate to the X-ray tubes C2 and C4 for example, it being possible to set default settings for their power and the times of their activation and deactivation, as well as the gantry, it being possible to set default settings for its rotation speed, as well as table advance.

Since the control and computation unit C10 has an input console, a user or operator of the CT device C1 can input measurement parameters, which then control data acquisition in the form of acquisition control signals AS. Information about currently used measurement parameters can be displayed on the screen of the control and computation unit C10; further information of relevance for the operator can additionally be displayed.

The projection measurement data p and/or raw data acquired by the detector C3 and/or C5 is transmitted by way of a raw data interface C23 to the control and computation unit C10. This raw data p is then further processed in an image reconstruction component C21, optionally after suitable preprocessing. The image reconstruction component C21 in this exemplary embodiment is realized in the control and computation unit C10 in the form of software on a processor, e.g. in the form of one or a number of the computer program codes $Prg_1$ to $Prg_n$. With regard to image reconstruction, as already described with regard to the control of the measurement process, the computer program codes $Prg_1$ to $Prg_n$ can also be contained on an external storage medium and can be loaded into the control and computation unit C10 as required. It is further possible for control of the measurement process and image reconstruction to be performed by different computation units.

The image data f reconstructed by the image reconstruction component C21 is then stored in a memory C22 of the control and computation unit C10 and/or output in the usual manner on the screen of the control and computation unit C10. It can also be fed by way of an interface (not shown in FIG. 1) into a network connected to the computed tomography system C1, for example a radiological information system (RIS), and stored in a mass storage unit accessible there or output as images.

The control and computation unit C10 can also execute the function of an EKG, a line C12 being used to derive the EKG potentials between patient and control and computation unit C10. The CT system C1 shown in FIG. 1 also has a contrast agent injector C11, by way of which contrast agent can additionally be injected into the blood circulation system of the patient, in order to display for example the vessels of the patient, in particular the ventricles of the beating heart, more clearly. It is also possible here to perform perfusion measurements, for which the proposed method is likewise suitable.

Figure 2:
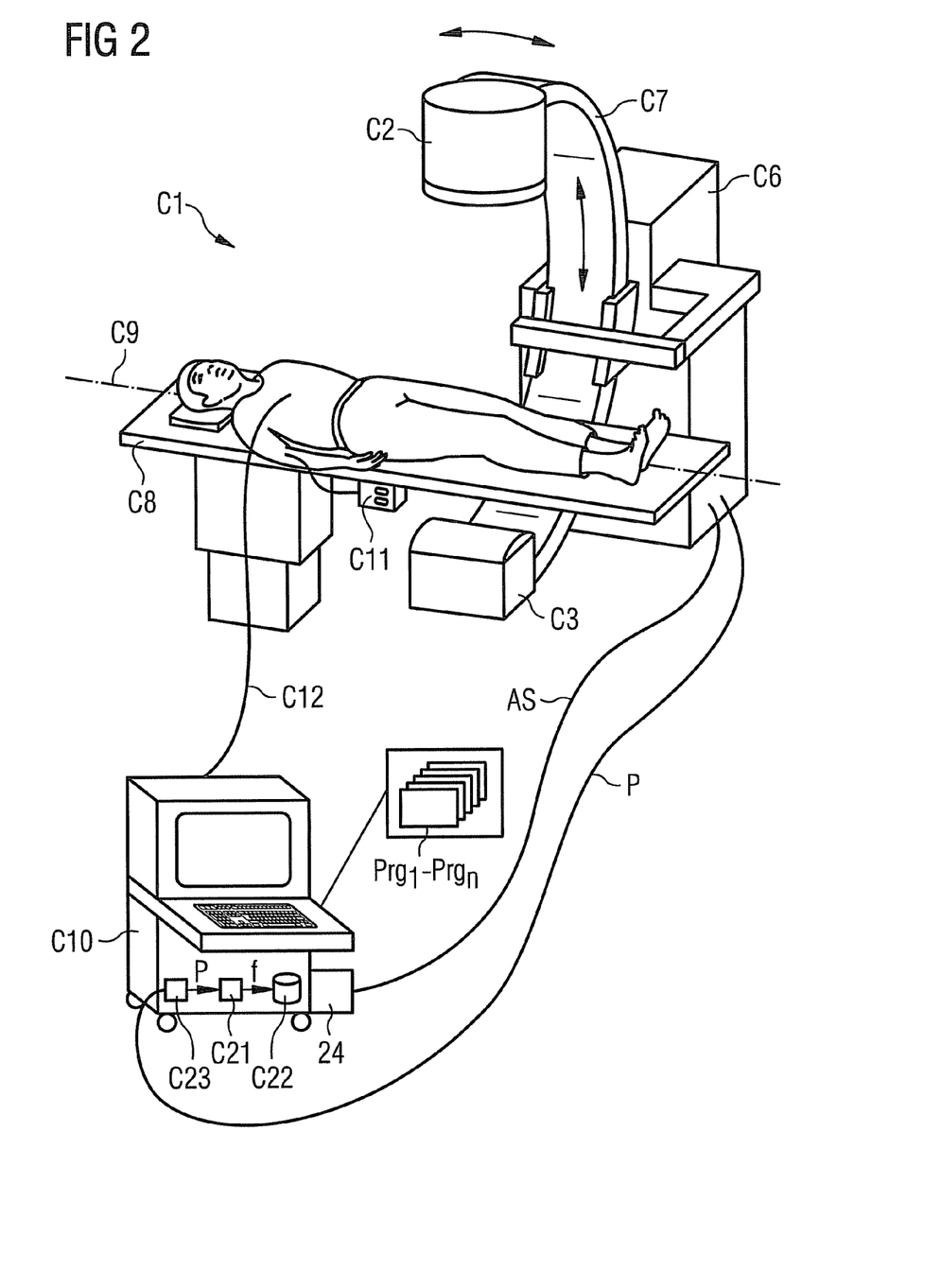
FIG. 2: shows a second schematic diagram of an example embodiment of a computed tomography system having an image reconstruction component.

FIG. 2 shows a C-arm system, wherein in contrast to the CT system in FIG. 1 the housing C6 supports the C-arm C7, to which both the X-ray tube C2 and the detector C3 opposite it are fastened. The C-arm C7 is also pivoted about a system axis C9 for a scan, so that a scan can take place from a plurality of scan angles and corresponding projection data p can be determined from a plurality of projection angles. Like the CT system in FIG. 1 the C-arm system C1 in FIG. 2 has a control and computation unit C10 of the type described in relation to FIG. 1.

Figure 3:
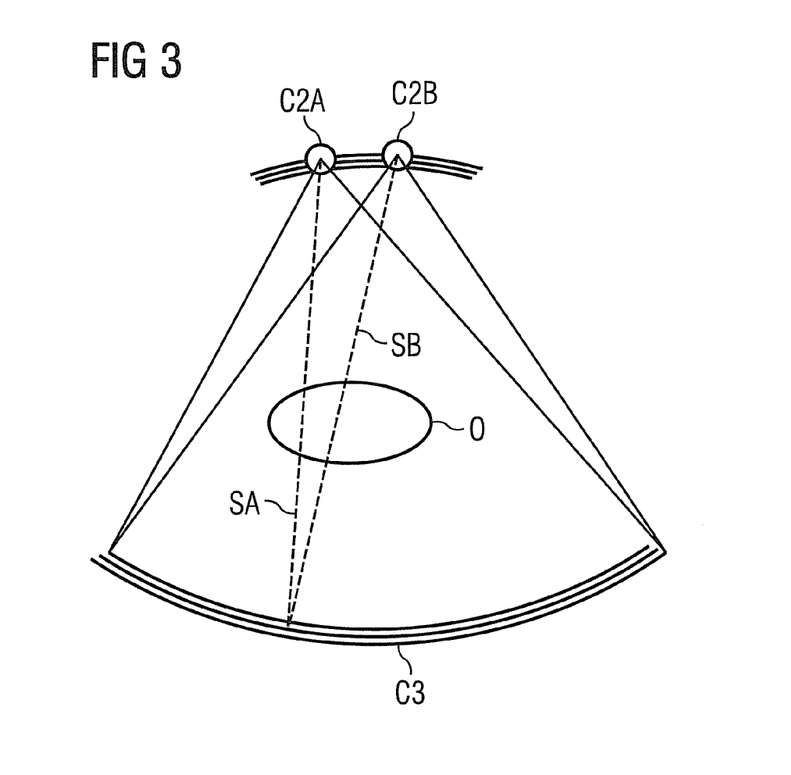
FIG. 3: shows a recording geometry.

An embodiment of the invention can be used in both the systems shown in FIGS. 1 and 2, subject to the changes to recording geometry explained in relation to FIG. 3. It can also in principle be employed for other CT systems, e.g. for CT systems having a detector forming a complete ring.

An embodiment of the invention is described below with reference to a cardio CT examination, i.e. the mapping of the human heart with a CT device. It is however not restricted to such recordings. In principle it is desirable when examining a patient using a CT system only to expose the patient to a small radiation dose. Cardio CT has developed in the meantime in such a manner that the dose applied to the patient has been reduced drastically. While dose values of 10 mSv were previously the norm, values of approx. 2 mSv have become possible in the meantime.

To enhance image quality a greater effective charge per CT image would be advantageous. The effective charge here is understood to be the product of the tube current and the irradiation time during data acquisition. This implies a higher dose for the patient. However since this has been reduced drastically as described above, a slight increase would be acceptable for the increase in the quality of the CT images.

An increase in the effective charge per CT image can be achieved both by increasing the output of the X-ray tube and by increasing the exposure time. The latter is not possible with cardio CT due to the associated deterioration in temporal resolution, as a longer measurement time means more heart movement during measurement, thereby increasing motion artifacts and reducing temporal resolution.

The tube output, i.e. the number of X-ray quanta of a certain energy emitted per unit of time; is predetermined by the tube current. This can only be increased up to a certain maximum value. Power values up to 120 kW can typically be achieved with high-power tubes. The development of X-ray tubes with much higher power values seems at present not to be technically feasible. An increase in the tube current could cause the anode plate, which is generally made of tungsten, to be damaged or destroyed due to the exceeding of a maximum temperature that can be tolerated by the material.

To increase the effective charge it is proposed that measurement be performed with a modified recording geometry, as shown in FIG. 3. Two X-ray sources C2A and C2B are employed. These are adjacent to one another; this means that radiation from both X-ray sources C2A and C2B strikes the same detector element of the detector C3 opposite. The two emitters C2A and C2B therefore illuminate the detector field together and simultaneously. This is shown with the two beams SA and SB, the beam SA leaving the X-ray source C2A and the beam SB leaving the X-ray source C2B. The two beams SA and SB respectively pass the examination object O, but because of the different positions of the two X-ray sources C2A and C2B on a different path and/or through different volume elements of the examination object O. The signal of a detector element is therefore made up of the sum of a number of non-identical line integrals.

The two X-ray sources C2A and C2B can be realized differently:

There are non-mechanical CT devices, in which the X-ray source does not rotate while data is being acquired. These have a flat X-ray source, which emits X-ray radiation from different parts of its surface in succession. One example is an arrangement of carbon nanotubes, in other words extended tubes of only around one nanometer diameter, made up of numerous linked rings of six carbon atoms each, which function as field effect transistors and emit X-ray quanta. Other types of inverse CT device, i.e. systems with a small detector and an extended X-ray source, are also suitable. With such flat X-ray sources it is possible to increase the radiation power by simultaneous activation of a number of matrix elements of the source.

With third-generation CT devices, as shown in FIG. 1, a number of traditional X-ray tubes disposed adjacent to one another are employed to achieve the recording geometry in FIG. 3.

With traditional image reconstruction methods, e.g. Feldkamp-based methods, the problem arises with a measurement geometry with a number of X-ray sources that the back projection of a detector signal is no longer unique, as the signal of a detector element represents a sum of a number of different line integrals, as shown in FIG. 3. It is not possible to split the detector signal into parts associated with the different X-ray sources.

Traditional reconstruction algorithms fail due to this lack of uniqueness. It is therefore proposed that the reconstruction problem resulting from the irradiation of a detector with a number of X-ray sources should be resolved by means of an iterative image reconstruction.

Figure 4:
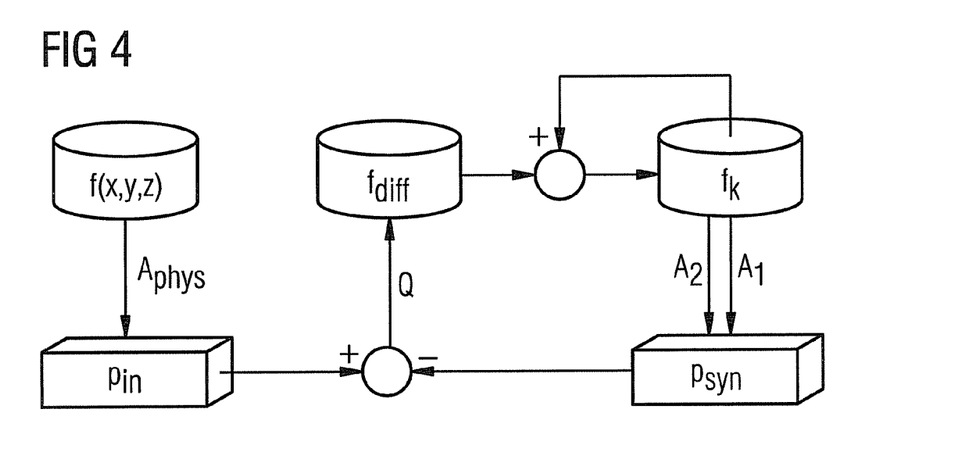
FIG. 4: shows a diagram of an iterative algorithm.

The basic principle of an iterative CT image reconstruction is illustrated in FIG. 4. The input data $p_{in}$ is the recorded projections. This is obtained—mathematically speaking—by applying the actual projector $A_{phys}$, in other words the, one present in reality, to the actual attenuation distribution f(x,y,z) of the examination object: $p_{in}=A_{phys} f(x,y,z)$. The purpose of the iterative algorithm is to determine from the input data $p_{in}$ an attenuation distribution f, i.e. a two-dimensional sectional image or a three-dimensional volume distribution of the attenuation, which corresponds as closely as possible to the actual attenuation distribution f(x,y,z) of the examination object.

The operators $A_1$ and $A_2$, constructed projectors, are intended to simulate the measurement process as accurately as possible. The projectors $A_1$ and $A_2$ are models of the projector $A_{phys}$ present in reality, i.e. the measurement process. The projector $A_1$ models the beam geometry in relation to the X-ray source C2A, and the projector $A_2$ models the beam geometry in relation to the X-ray source C2B; both projectors $A_1$ and $A_2$ project onto the same detector. If more than two X-ray sources are used instead of the geometry according to FIG. 3, the corresponding number of projectors $A_i$ is also employed. Variables incorporated in the operators $A_1$ and $A_2$ are for example a model of the tube focus, the detector aperture, detector crosstalk, etc., . . . .

One example of suitable projectors $A_i$ is what is known as the Josephson projector. Here line integrals are modeled by needle beams, i.e. beams with zero extension. Every vertex, in other words every volume element, of the image volume is linked to a base function, e.g. in a trilinear manner, so that the contribution of the vertex to the line integral can be interpolated accordingly. The respective integral is then input as a projection value into the respective detector bin. Such operators are known per se and described for example in P. M. Joseph, "An improved algorithm for reprojection rays through pixel images", IEEE Trans. Med. Imag. 1:193-196, 1982, the entire contents of which are hereby incorporated herein by reference.

Further projectors are described for example in K. Mueller, R. Yagel, J. J. Wheller: "Fast implementations of algebraic methods for three-dimensional reconstruction of cone-beam data", IEEE Trans. Med. Imag. 18 (6): 538-548, 1999, the entire contents of which are hereby incorporated herein by reference.

The sectional image, i.e. the calculated attenuation distribution, is obtained by the operator Q from the projections:

$$f = Q\, p \cdot Q = A^T := +A_2)^T \text{ applies.}$$

The back projector Q represents a non-exact reconstruction method. The 3-dimensional radon transformation required for an exact resolution is therefore not performed completely. For this reason and because of the lack of uniqueness explained above due to the number of X-ray sources, applying the back projector Q to the input data $p_{in}$ only determines the actual attenuation distribution $f(x,y,z)$ approximately. The iterative procedure is therefore used to approximate as closely as possible to the actual attenuation distribution $f(x,y,z)$ within a number of iteration cycles.

A first attenuation distribution $f_0$ is calculated by means of an initial reconstruction, i.e. by a first application of the back projector Q to the input data $p_{in}$; this is the first estimated image. This is not shown in FIG. 4. $f_0$ corresponds to the variable $f_k$ in FIG. 4 in the zeroth iteration cycle. Before the back projector Q is first applied to the input data $p_{in}$ it is possible to perform a rebinning step. This re-orders measurement data acquired in cone or fan beam geometry, so that it is present as though it were measured in parallel beam geometry.

Following the first back projection synthetic projections are calculated with the projectors $A_1$ and $A_2$: $P_{syn} = A\, f_0 := A_1 f_0 + A_2 f_0$. A here is the operator, resulting from the application of $A_1$ and $A_2$. A simultaneous forward projection therefore results along the connecting lines between the X-ray sources C2A and C2B and the respective detector element. Synthetic means that it is not measured data but a calculated variable.

The difference between the input data $p_{in}$ and the synthetic projections $P_{syn}$ is then determined. This residue $p_{in}-P_{syn}$ is in turn used to calculate a new attenuation distribution using the back projector Q, namely the differential attenuation distribution $f_{diff}$; $f_{diff} = Q\,(p_{in}-P_{syn})$. The difference $p_{in}-P_{syn}$ is thus back projected with the operator Q, to calculate the residual image $f_{diff}$.

The addition of the differential attenuation distribution $f_{diff}$ and the attenuation distribution $f_0$ calculated in the zeroth iteration cycle produces an improved attenuation distribution $f_1$. This corresponds in FIG. 4 to the variable $f_k$ of the first iteration cycle. The described procedure is iterated from this point on. In each iteration cycle therefore the newly calculated data $P_{syn}$ is compared with the measured data $p_{in}$. As a result the iteration image $f_k$ is aligned more closely to the measurement data in every iteration cycle.

It is possible for this iterative method not to result in convergence. Therefore instead of the simple addition of $f_{diff}$ and $f_k$ a regularization function is first applied to $f_k$ and the resulting regularization term is added to $f_{diff}$. The regularization term is therefore $R\,f_k$, where R is a non-linear operator applied to the image $f_k$. The regularization function R is non-linear and has the task of stabilizing resolution. For example R can smooth noise in the image $f_k$.

To express the described iterative procedure mathematically, the iteration equation can be realized with the aid of the steepest descent method. For this $z(f)$ is defined as the cost function of the attenuation distribution to be minimized:

$$z(f) = \|Af - p_{in}\|_K^2 + R \cdot f \qquad \text{Formula (1)}$$

The scalar product here is defined as follows:

$$\|Af - p_{in}\|_K^2 = (Af - p_{in})^T \cdot K \cdot (Af - p_{in}) \qquad \text{Formula (2)}$$

K is a matrix operation, namely a convolution operation with a conventional CT reconstruction kernel and/or reconstruction filter.

R is the non-linear regularization function and can be as follows for example when applied to the image f:

$$\beta \cdot \sum_{i,j}^{N} d_{i,j} \cdot V(f_i - f_j) \qquad \text{Formula (3)}$$

In this instance the regularization term $$R(f) = \beta \cdot \sum_{i,j}^{N} d_{i,j} \cdot V(f_i - f_j)$$

links the CT values $f_i$ and $f_j$ of adjacent pixels to index i and j and to inverse distance $1/d_{i,j}$ with the aid of the potential function V. This regularization term allows certain conditions to be forced between the values of adjacent pixels.

Forming the gradient of the cost function allows the iteration equation to be produced:

$$(f)_{k+1} = (f)_k \alpha \cdot \text{grad}_f(z) \qquad \text{Formula (4)}$$

The following therefore results for the iteration equation and/or update equation:

$$\begin{aligned} f_{k+1} &= f_k + \alpha \cdot Q \cdot K \cdot (p_{in} - A \cdot f_k) + R(f_k) \qquad \text{Formula (5)}\\ &= f_k + \alpha \cdot (A_1 + A_2)^T \cdot K \cdot (p_{in} - A \cdot f_k) + R(f_k) \\ &= f_k + \alpha \cdot (A_1^T \cdot K \cdot (p_{in} - A \cdot f_k) + A_2^T \cdot K \cdot (p_{in} - A \cdot f_k)) + \\ &\quad R \cdot f_k \end{aligned}$$

As an alternative to the method for minimizing a cost function it is possible to arrive at this update equation differently, e.g. using the Landweber method, for which, see L. Landweber: An iteration formula for fredholm integral equations of the first kind. American Journal of Mathematics 73(3): 615-624, 1951, the entire contents of which are hereby incorporated herein by reference.

The implementation of the iterative algorithm explained by way of example using the formulas (1) to (5) can be performed using methods known per se. It is essential that the projector A contains the components $A_1$ and $A_2$, so that it simulates the measurement geometry of the use of a number of X-ray sources.

The invention was described above using an example embodiment. It is evident that numerous changes and modifications are possible without departing from the scope of the invention. In particular a number of adjacent X-ray sources can be employed instead of two.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, non-transitory computer readable medium and non-transitory computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory storage medium or non-transitory computer readable medium, is adapted to store information and is adapted to interact with a data processing facility or computer device to execute the program of any of the above mentioned embodiments and/or to perform the method of any of the above mentioned embodiments.

The non-transitory computer readable medium or non-transitory storage medium may be a built-in medium installed inside a computer device main body or a removable non-transitory medium arranged so that it can be separated from the computer device main body. Examples of the built-in non-transitory medium include, but are not limited to, rewriteable non-volatile memories, such as ROMs and flash memories, and hard disks. Examples of the removable non-transitory medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing image data of an examination object from measurement data of a computed tomography system, the method comprising:
    irradiating the examination object by a number of X-ray sources simultaneously while acquiring the measurement data such that different projections of the examination object associated with the number of X-ray sources is acquired by one detector element, each of the number of X-ray sources irradiating the examination object in its entirety;
    determining different iteration images of the examination object, one after the other, from the measurement data by use of an iterative algorithm; and
    employing a computation operation with the iterative algorithm, which is applied to the different iteration images, taking the presence of the number of X-ray sources into account, the computation operation including at least one operator, which maps measurement geometry while the measurement data is being acquired, the measurement geometry including first relative positions of the number of X-ray sources to one another and second relative positions of the number of X-ray sources to the detector.

2. The method as claimed in claim 1, wherein the computation operation is employed to calculate projection data from respective ones of the iteration images.

3. The method as claimed in claim 2, wherein the calculated projection data is linked to the measurement data.

4. The method as claimed in claim 3, further comprising:
    calculating image data from the linking of the projection data to the measurement data.

5. The method as claimed in claim 4, wherein the calculated image data is linked to the iteration image of the previous iteration.

6. The method as claimed in claim 5, wherein before linking the calculated image data and the iteration image of the previous iteration, a non-linear regularization function is applied to the iteration image of the previous iteration.

7. The method as claimed in claim 5, wherein the computation operation calculates the projection data is calculated based on the linking of the image data to the iteration image of the previous iteration.

8. The method as claimed in claim 1, wherein the number of X-ray sources move around the examination object while the measurement data is being acquired.

9. The method as claimed in claim 1, wherein the number of X-ray sources are produced by activating a number of elements of an X-ray source.

10. The method as claimed in claim 1, wherein the irradiating the examination object includes irradiating the examination object simultaneously by two X-ray sources.

11. A control and computation unit for controlling reconstruction of image data of an examination object from measurement data of a CT system, the control and computation unit comprising:
    a program memory to store program code, the program code, when executed, causing the control and computation unit to:
        irradiate the examination object by a number of X-ray sources simultaneously while acquiring the measurement data such that different projections of the examination object associated with the number of X-ray sources is acquired by one detector element, each of the number of X-ray sources irradiating the examination object in its entirety;
        determine different iteration images of the examination object, one after the other, from the measurement data by use of an iterative algorithm; and
        employ a computation operation with the iterative algorithm, which is applied to the different iteration images, taking the presence of the number of X-ray sources of the CT system into account, the computation operation including at least one operator, which maps measurement geometry while the measurement data is being acquired, the measurement geometry including first relative positions of the number of X-ray sources to one another and second relative positions of the number of X-ray sources to the detector.

12. A CT system comprising:
    the control and computation unit as claimed in claim 11.

13. The control and computational unit as claimed in claim 11, wherein the control and computation unit employs the computation operation to calculate projection data from respective ones of the iteration images.

14. The control and computational unit as claimed in claim 13, wherein the calculated projection data is linked to the measurement data.

15. The control and computational unit as claimed in claim 14, wherein the control and computation unit calculates image data from the linking of the projection data to the measurement data.

16. The control and computational unit as claimed in claim 15, wherein the calculated image data is linked to the iteration image of the previous iteration.

17. The control and computational unit as claimed in claim 16, wherein before linking the calculated image data and the iteration image of the previous iteration, a non-linear regularization function is applied to the iteration image of the previous iteration.

18. A non-transitory computer readable medium including program segments for, when executed on a computer device, causing the computer device to implement the method of claim 1.

* * * * *